United States Patent [19]

Osborne et al.

[11] Patent Number: 4,612,377

[45] Date of Patent: Sep. 16, 1986

[54] PREPARATION OF 2-CHLORO-5-METHYLPYRIDINE

[75] Inventors: Robert Osborne; Kevin D. Bailey, both of Clackmannanshire, Scotland

[73] Assignee: Imperial Chemical Industries PLC, London, England

[21] Appl. No.: 589,232

[22] Filed: Mar. 14, 1984

[30] Foreign Application Priority Data

Mar. 30, 1983 [GB] United Kingdom ............ 8308822

[51] Int. Cl.$^4$ ............................................ C07D 211/72
[52] U.S. Cl. .................................................. 546/345
[58] Field of Search ............................. 546/345, 346

[56] References Cited

U.S. PATENT DOCUMENTS

| | | |
|---|---|---|
| 3,123,608 | 3/1964 | Mathes et al. ............ 546/346 |
| 4,205,175 | 5/1980 | Bowden et al. ............ 546/345 |
| 4,473,696 | 9/1984 | Hartmann et al. ............ 546/290 |

*Primary Examiner*—Henry R. Jiles
*Assistant Examiner*—Robert C. Whittenbaugh
*Attorney, Agent, or Firm*—Cushman, Darby & Cushman

[57] ABSTRACT

A 2-oxo-5-methyl-5,6-dihalopiperidine is contacted in a high boiling solvent, preferably trichlorobenzene, with a stoichiometric excess, up to 70 mole % excess, of a chlorinating agent, preferably phosphorus oxychloride or phosgene, at an elevated temperature between 80° and 130° C. The solution of 2-chloro-5-methylpyridine so obtained may be used directly for further chlorination to form 2-chloro-5-trichloromethylpyridine with, for example, chlorine gas in the presence of a free radical initiator. This chemical intermediate is useful in the synthesis of certain herbicidal compounds.

5 Claims, No Drawings

PREPARATION OF 2-CHLORO-5-METHYLPYRIDINE

This invention relates to a process for the preparation of 2-chloro-5-methylpyridine which is useful as an intermediate in the synthesis of certain herbicides.

Various 4-(5-halomethyl-2-pyridyloxy)-phenoxy compounds are known to be useful as herbicides as can be seen from European Pat. Nos. 483 and 1473. For example, butyl 2-[4-(5-trifluoromethyl-2-pyridyloxy)-phenoxy]propionate, known generically as fluazifopbutyl, is an effective grass herbicide which can be used in the cultivation of broad-leaved crops such as cotton and soyabeans. A material used in the preparation of this compound is 2-chloro-5-trichloromethylpyridine which may be prepared by the chlorination of 2-chloro-5-methylpyridine, itself obtained by the chlorination of beta-picoline.

In pending U.S. Ser. No. 433,273, filed 7th Oct. 1982 and assigned to the applicants' subsidiary company, ICI Americas Inc., an alternative method of preparing 2-chloro-5-trichloromethylpyridine is described which obviates the use of beta-picoline and associated problems of unwanted byproduct formation during its chlorination to form 2-chloro-5-methylpyridine. In the method described in U.S. Ser. No. 433,273, 2-chloro-5-methylpyridine is obtained by condensing propionaldehyde and an acrylic ester to form a 4-formylpentanoate ester which may then be aminated with a nitrogen source such as an amine or ammonium compound to form 5-methyl-3,4-dihydro-2(1H)-pyridone. The dihydropyridone is halogenated, dehydrohalogenated to form 2-hydroxy-5-methyl-6-pyridine (or its tautomer 5-methyl-2(1H)-pyridone), and then chlorinated to give 2-chloro-5-methylpyridine.

Halogenation of the dihydropyridone may be accomplished with a halogenating agent such as chlorine, bromine, sulphuryl chloride or sulphuryl bromide, in which case halogen atoms are added across the double bond of the pyridone ring to form a dihalo compound of the formula (I):

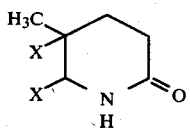
(I)

in which X is halogen such as chloro or bromo. Dehydrohalogenation of the dihalo compound of formula (I) by heating it to a temperature of 100° to 170° C., optionally in the presence of a high boiling solvent, affords the pyridine of formula (II):

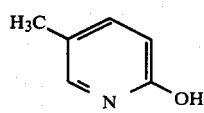
(II)

which can then be chlorinated to give 2-chloro-5-methylpyridine. Thus, the preparation of 2-chloro-5-methylpyridine from the dihalo compound of formula (I) proceeds in two steps, viz. dehydrohalogenation to form the pyridine of formula (II) followed by chlorination of the pyridine.

The present invention is a modification of the method described in U.S. Ser. No. 433,273, and is directed towards the preparation of 2-chloro-5-methylpyridine from the dihalo compound of formula (I) in a single step.

According to the present invention there is provided a process for the preparation of 2-chloro-5-methylpyridine having the formula (III):

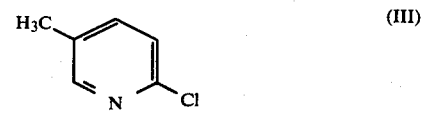
(III)

which comprises contacting a dihalo compound of the formula (I):

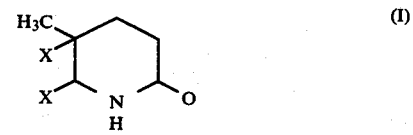
(I)

in which X is halogen, such as chloro or bromo, with a chlorinating agent at an elevated temperature.

Of particular interest as the dihalo compound of formula (I) is 2-oxo-5-methyl-5,6-dichloropiperidine.

The chlorinating agent is preferably phosphorus oxychloride or phosgene but other chlorinating agents may be used. To maximise product yield, the chlorinating agent is used in stoichiometric excess, up to 70 mole %, preferably about 50%, excess over the dihalo compound of formula (1), and introduced into a solution of the dihalo compound in a high boiling solvent such as aromatic hydrocarbon solvent, for example toluene or xylene, or a halogenated aromatic hydrocarbon, for example chlorobenzene, o-dichlorobenzene and preferably 1,2,4-trichlorobenzene. The solution of the dihalo compound is heated to an elevated temperature of between 80° and 130° C., ideally about 120° C., and the chlorinating agent introduced during a period of from 0.5 to 10 hours, typically from 1 to 2 hours. Alternatively, the dihalo compound may be added to the chlorinating agent; for example, a solution of the dihalo compound in trichlorobenzene is conveniently added to refluxing phosphorus oxychloride. After addition of the chlorinating agent, the solution is beneficially maintained at an elevated temperature for a further period of time the duration of which will depend on the addition time of the chlorinating agent. As a guide, when a 50 mole % excess of phosphorus oxychloride is passed into a solution of 2-oxo-5-methyl-5,6-dichloropiperidine in 1,2,4-trichlorobenzene at 120° C. over 1 to 2 hours, the solution is preferably held at that temperature for a further 5 to 6 hours after the addition of the phosphorus oxychloride is complete.

The solution of 2-chloro-5-methylpyridine so obtained may be used directly for further chlorination to form 2-chloro-5-trichloromethylpyridine by, for example, passing chlorine gas through the solution in the presence of a free radical initiator such as benzoyl peroxide, or may first be washed, before chlorination, by drowning into aqueous alkali and adjusting the pH to near neutrality, and then separating from the aqueous layer.

The dihalo compound of formula (I) may be obtained by the chlorination of 5-methyl-3,4-dihydro-2(1H)-pyridone, conveniently by passing chlorine gas through a solution of the dihydropyridone in a suitable organic solvent at a temperature of 50° to 60° C. The solution of the dihalo compound so obtained may be used directly in the process of the present invention. In this case it is preferred to conduct the chlorination of the dihydropyridine in 1,2,4-trichlorobenzene which is the preferred solvent for the process of the invention. 1,2,4-Trichlorobenzene is also preferred as the solvent for the chlorination of the 2-chloro-5-methyl-pyridine side chain.

5-Methyl-3,4-dihydro-2(1H)-pyridone is obtained as described in U.S. Ser. No. 433,273 and, by way of illustration, in the following Reference Examples 1 to 4 which form no part of the present invention.

The invention is, however, illustrated but not limited by, Examples 1 and 2 in which in these and Reference Examples 1 to 4 percentages are by weight unless otherwise stated and the following abbreviations are used:

| | |
|---|---|
| °C. | degrees Centigrade |
| ml | milliliters |
| g | grams |
| m | moles |
| mmoles | millimoles |
| mm | millimeters |
| GLC | gas liquid chromatography |
| GC/MS | gas chromatograph-mass spectrometry |
| IR | infra red |
| NMR | nuclear magnetic resonance |
| mp | melting point |
| bp | boiling point |
| $d_6$-DMSO | deuterated dimethyl sulphoxide |
| MCB | monochlorobenzene |
| DHP | 5-methyl-3,4-dihydro-2(1H)—pyridone |
| HMP | 2-hydroxy-5-methylpyridine |
| CMP | 2-chloro-5-methylpyridine |
| CCMP | 2-chloro-5-trichloromethylpyridine |
| dichloro-DHP | 2-oxo-5-methyl-5,6-dichloropiperidine |
| HPLC | high pressure liquid chromatography |
| TCB | 1,2,4-trichlorobenzene | and the conventional symbols for the chemical elements.

REFERENCE EXAMPLE 1

A 500 ml 4-neck flask was equipped with a stirrer, thermometer, addition funnel and condenser. To the flask was charged 191.7 g (2.2 m) of morpholine and 138.2 g (1 m) of potassium carbonate (anhydrous) and the mixture was stirred and cooled to −5° C. with an ice-salt bath. To the flask was added 58 g (1 m) of propionaldehyde over a period of 55 minutes at a pot temperature of −5° C. The temperature was then allowed to rise to 25° to 27° C. and the reaction was continued for 2 hours at 25° C. The product was filtered and the filter cake washed with four 15 ml washes of toluene. The filtrate was heated under vacuum while morpholine was stripped using a 1 foot Vigreux column. This treatment was carried out at an oil bath temperature of 85° to 112° C., a pot temperature of 70° to 90° C., a vapour temperature of 41° to 58° C. and at a pressure of approximately 35 to 40 mm of Hg. The vacuum stripping was carried out until 133.3 g of product was obtained as a residue. GLC and GC/MS established that the predominant product was 4-(2-propenyl)morpholine.

$^{13}$C NMR in $d_6$-DMSO (in δ units): 15.2 (CH$_3$); 95.1 (CH$_3$—CH)=; 140.8 (CH=CH—); 49.4 (—N(—CH$_2$—)$_2$); and 66.1 (O(—CH$_2$—)$_2$).

REFERENCE EXAMPLE 2

A solution of 40 g of crude morpholinopropene produced in Reference Example 1 in 175 ml of acetonitrile is cooled to −2° C. in an ice-salt bath and treated with a solution of 30.5 g (0.35 m) of methylacrylate in 70 ml of acetonitrile dropwise over a period of 20 minutes at −2° C. to 0° C. The temperature of the solution is then gradually raised and held at 66° to 76° C. for 17 hours. At that point, a predominate product peak can be detected by GLC together with a smaller unidentified peak while at the same time, the morpholinopropene peak has almost completely disappeared. The methyl 3-methyl-2-(4-morpholinyl)cyclobutane carboxylate was characterised by GC/MS and NMR.

$^{13}$C NMR in $d_6$-DMSO (in δ units): 66.3 (O(—CH$_2$—)$_2$); 50.2 (—N(—CH$_2$—)$_2$); 70.8 (N—CH); 31.0 (CH$_3$—CH); 26.2 (cyclobutane—CH$_2$—); 39.1 (CH—COOCH$_3$); 174.1 (—COOCH$_3$); 51.4 (—COOCH$_3$); and 20.6 (CH—CH$_3$).

REFERENCE EXAMPLE 3

A solution of 18 g (0.3 m) of acetic acid in 120 ml of water is added to the crude morpholino cyclobutane carboxylate ester product of Reference Example 2 and the reaction mixture is heated at 70° to 79° C. for 5 hours. The product solution is cooled to room temperature, diluted with 150 ml of water and extracted 3 times with ethyl acetate, 100 ml each wash. The extracts were washed 2 times with dilute sodium chloride brine solution and methyl 4-formylpentanoate is obtained after vacuum stripping at 60° to 70° C. and a moderate vacuum of 100 mm to 28 mm of Hg in a yield of 29.2 g.

The crude methyl 4-formylpentanoate obtained above was purified by distillation at 83° to 85° C. at 6 mm to 8 mm of Hg with 90% recovery. Purity by GLC after distillation was determined to be 95.3% and the product was characterised by IR, NMR and GC/MS.

$^{13}$C NMR in $d_6$-DMSO (in δ units): 51.4 (—COOCH$_3$); 173.2 (—COOCH$_3$); 31.0 (—CH$_2$—COOCH$_3$); 25.4 (—CH$_2$—CH$_2$—COOCH$_3$); 45.1 (CH—CH$_3$); 13.0 (CH—CH$_3$); and 204.7 (—CHO).

REFERENCE EXAMPLE 4

To 1.44 g (0.01 m) of methyl 4-formylpentanoate dissolved in 10 ml of acetic acid was added 1.54 g (0.02 m) of ammonium acetate and the mixture was heated at 80° to ±15° C. for 16 hours. GLC showed about 11% unreacted starting material, 89% of the desired title product and no by-products. The product was vacuum stripped, dissolved in 10 ml of ethyl acetate and washed 4 times with water, 2.5 ml each wash. The product was distilled after vacuum stripping of ethyl acetate to yield 0.5 g of 5-methyl-3,4-dihydro-2(1H)-pyridone (DHP), bp 103° C. at 0.5 mm of Hg. The product was recrystallised from ethyl acetate, mp 76° to 78° C. Element Analysis: N 12.13% (Calculated 12.8%).

$^{13}$C NMR in $d_6$-DMSO (in δ units): 19.0 (CH$_3$); 169.0 (C=O); 30.1 (CH$_2$ alpha to C=O); 25.5 (CH$_2$ beta to C=O); 112.0 (C(CH$_3$)=CH); and 120.3 (CH directly attached to NH).

EXAMPLE 1

Preparation of CMP from DHP 108 g of a solution containing 27.8 g (0.25 m) of DHP in TCB were placed in a flask and chlorine gas was passed into the solution at such a rate that the temperature was held between 50° and 60° C. On completion of the reaction (judged by a colour change and a test for free chlorine in solution) the solution of dichloro-DHP was heated to 122° C. and 65.2 ml (0.425 m) phosphorus oxychloride run in over 30 minutes. The resulting dark brown solution was held for 6.5 hours before being run into 350 ml water containing 180 ml of 30% sodium hydroxide solution. The pH of the mixture was adjusted to 6.5 with a small amount of sulphuric acid and allowed to separate into two layers. 92 g of organic layer were thus obtained and found to contain 28.2% CMP (HPLC analysis) giving a yield of 81.3% based on the DHP starting material.

EXAMPLE 2

Preparation of CCMP from DHP

A solution of DHP (25 g; 0.225 m) in TCB (51 ml; 75 g) warmed to 50° C. in a flask was chlorinated with chlorine gas as described in Example 1. After chlorination, the pale green solution so obtained was heated to 100° C. and phosphorus oxychloride (36.2 g; 22 ml) added over 30 minutes. The temperature was raised to 110° C. and side chain chlorination commenced. Benzoyl peroxide (12 g) in TCB (100 ml) was added at a rate of approximately 0.2 ml/minute while chlorine gas (75 g) was passed through the solution turning it orange.

After being left to cool overnight, the reaction mass was heated to 50° C., 75 ml concentrated hydrochloric acid added and the contents removed from the flask. A further 100 ml of concentrated hydrochloric acid was used to dissolve and extract sticky material remaining in the flask. The combined hydrochloric acid extracts (approx. 200 ml) were separated from the organic layer and diluted with approximately 500 ml water to produce a yellow solid which was dried in a dessicator overnight yielding 25.8 g of a yellow sugary product identified as CCMP. Residual CCMP remaining in the organic layer was extracted with 75% vol/vol sulphuric acid to give semi-fluid sticky ball on drown-out.

The final material was found to contain 84.98% CCMP by GC analysis, equivalent to a yield of 42% on DHP.

We claim:

1. A process for the preparation of 2-chloro-5-methylpyridine having the formula (III):

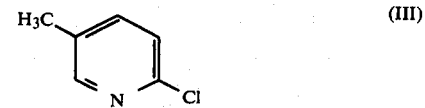

which comprises contacting a dihalo compound of the formula (I):

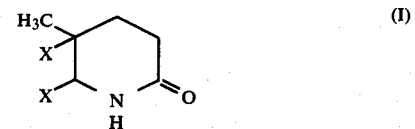

in which X is halogen, with a chlorinating agent selected from the group consisting of phosphorus oxychloride and phosgene at an elevated temperature of 80° to 130° C. in a high boiling chlorinated aromatic hydrocarbon solvent which is liquid at the temperature employed, the chlorinating agent being used in stoichiometric excess, up to 70 mole %, over the dihalo compound (I).

2. A process according to claim 1 in which the high boiling solvent is 1,2,4-trichlorobenzene.

3. A process for the preparation of 2-chloro-5-trichloromethyl pyridine which comprises contacting in a high boiling chlorinated aromatic hydrocarbon solvent which is liquid at the temperature employed, the dihalo compound (I) of claim 1 with a chlorinating agent selected from the group consisting of phosphorus oxychloride and phosgene at an elevated temperature of 80° to 130° C., the chlorinating agent being used in stoichiometric excess, up to 70 mole %, over the dihalo compound (I) and further chlorinating the 2-chloro-5-methylpyridine so obtained.

4. A process according to claim 3 in which the 2-chloro-5-methylpyridine is further chlorinated with chlorine gas in the presence of a free radical initiator.

5. A process according to claim 3 in which the high boiling solvent is 1,2,4-trichlorobenzene.

* * * * *